United States Patent [19]

Gergely

[11] Patent Number: 4,459,024
[45] Date of Patent: Jul. 10, 1984

[54] METHOD AND APPARATUS FOR LIGHT DETECTION AND RANGING FOR USE IN VISUALLY OBSTRUCTED AREAS

[75] Inventor: John S. Gergely, Ponca City, Okla.

[73] Assignee: Conoco Inc., Ponca City, Okla.

[21] Appl. No.: 328,936

[22] Filed: Dec. 9, 1981

[51] Int. Cl.³ .............................................. G01N 21/00
[52] U.S. Cl. .................... 356/338; 250/227; 250/574; 250/575; 356/342
[58] Field of Search .............. 356/336, 338, 342, 343; 250/564, 574, 575, 578, 227

[56] References Cited

U.S. PATENT DOCUMENTS

| | | |
|---|---|---|
| 2,481,034 | 9/1949 | Neufeld . |
| 3,068,739 | 12/1962 | Hicks, Jr. et al. .............. 356/342 X |
| 3,317,730 | 5/1967 | Hilsum . |
| 3,384,885 | 5/1968 | Forbush .......................... 250/227 X |
| 3,458,651 | 7/1969 | Dryden . |
| 3,499,159 | 3/1970 | Carrier et al. . |
| 3,541,340 | 11/1970 | Binks ............................... 250/227 X |
| 3,899,688 | 8/1975 | Perieres . |
| 3,994,601 | 11/1976 | Brugger . |
| 3,998,552 | 12/1976 | Stewart et al. . |
| 4,058,736 | 11/1977 | Takahashi et al. . |
| 4,112,310 | 9/1978 | Malinowski . |
| 4,125,779 | 11/1978 | Malinowski . |
| 4,146,799 | 3/1979 | Pitt et al. .......................... 356/343 X |
| 4,152,025 | 5/1979 | Rellstab et al. .................. 250/575 X |
| 4,304,492 | 12/1981 | Fox .................................. 250/575 X |

Primary Examiner—William L. Sikes
Assistant Examiner—Matthew W. Koren
Attorney, Agent, or Firm—William J. Miller

[57] ABSTRACT

Apparatus for transmitting light and detecting resultant scattering in order to derive information relating to a light-scattering object. A fiberoptic cable has one end adjacent a light generator and the other end aimed at a light-scattering object. A receiver gathers light scattered by the object at which the light output of the cable is aimed. An information processor is connected to the receiver and is operative to generate values relating to properties of the light-scattering object.

5 Claims, 2 Drawing Figures

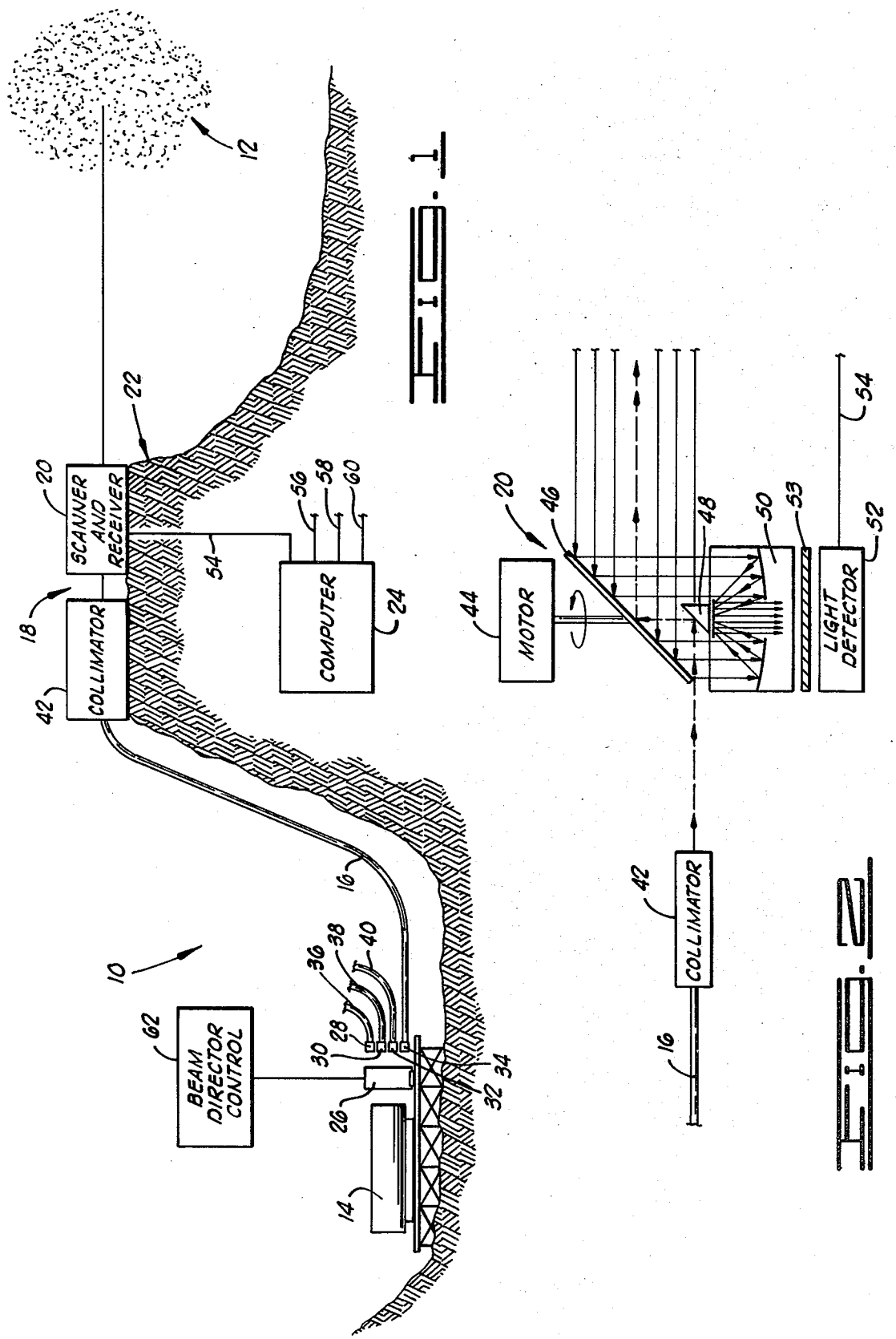

METHOD AND APPARATUS FOR LIGHT DETECTION AND RANGING FOR USE IN VISUALLY OBSTRUCTED AREAS

BACKGROUND AND SUMMARY OF THE INVENTION

This invention relates to light detection and ranging apparatus and methods.

Generally, light detection and ranging schemes have been used in the past to derive information relating to the concentration and spacial range, among other things, of particles suspended in air. Such systems have been used to monitor air pollution.

Past systems include a light source which is aimed at particles of interest. A light receiver detects light scattered by such particles and means are provided to derive information relating to the scattered light, e.g., its intensity and/or wavelength. From such parameters, time-varying information relating to particle concentration, type, size, and range, can be determined.

Past apparatus typically use a laser as a light source. In the case where pollution is being monitored, the laser light output is directed toward a portion of the sky, light is scattered by the pollution, and detected by a receiver. Some past apparatus have used a scanner which is basically a rotating mirror that repeatedly sweeps the laser beam, in a plane, about a 360° arc. When a scanner is utilized, the receiver thus detects light scattered from particles in a selected plane.

Such past monitoring permits particle detection only along a selected line or, when a scanner is used, in a selected plane. Such monitoring is impaired when an object, e.g., a hill, tree, building, etc., prevents projection of laser light beyond the object.

It is an object of the present invention to provide a method and apparatus for light ranging and detection for use in the presence of light-blocking objects.

It is a more specific object to provide such a method and apparatus which utilizes only one light source.

In a preferred embodiment of the invention, a plurality of fiberoptic cables are provided adjacent the light output of a laser. When the laser is generating light, the light travels in the cable and provides a light output at the other end, which is located and positioned to monitor a selected portion of the sky. A light receiver is associated with each cable end and serves to detect light backscattered by the ambient pollution. Each receiver is connected to a computer which generates values indicative of different parameters, e.g., particle concentration and spatial range, of each area. The computer is programmed to generate a three-dimensional time-varying map of the volume being mapped.

These and other objects and attendant advantages of the invention will be made apparent in view of the following drawings and detailed description of a preferred embodiment of the invention.

DESCRIPTION OF THE DRAWINGS

FIG. 1 is a schematic view of a portion of the instant embodiment of the invention.

FIG. 2 is an expanded, detailed view of a portion of the schematic in FIG. 1.

DETAILED DESCRIPTION OF THE INVENTION

Turning now to the drawings, indicated generally at 10 is a portion of the instant embodiment of the invention. The instant embodiment of the invention is used to monitor ambiant air pollution 12. Speaking now only generally of the operation of the instant embodiment of the invention, light from a laser 14 is transmitted through a fiberoptic cable 16 to a remote station, indicated generally at 18, which includes a scanner and receiver 20. The remote station is located on a hill 22. The light is radiated in the direction in which it is desired to monitor ambient air pollution. Pollution 12 backscatters light in the direction of the receiver in the form of fluorescence, raman, or the laser light itself. The scattered light is detected by scanner and receiver 20 and a signal is generated and provided to a computer 24. Evaluation of the signals by computer 24 provides information relating to the concentration and spacial range of ambient air pollution. The instant invention provides a new method and apparatus which utilizes existing light detection and ranging schemes to monitor ambient pollution levels, such schemes including raman, resonance raman, fluorescence, resonance fluorescene, longpath absorption, and differential absorption of scattered energy.

Examining more specifically the structure of the instant embodiment of the invention, included therein is a conventional switching beam-director 26. Beam-director 26 is operable to direct light radiation from laser 14 into a selected one of objective lenses 28, 30, 32, 34. Each objective lens serves to focus light output into a fiberoptic cable 36, 38, 40, 16, respectively, associated with each lens. Light energy is thus transmitted to various remote stations, like station 18. For a more detailed view of station 18 attention is directed to FIG. 2. Fiberoptic cable 16 terminates in a conventional collimator 42 which produces parallel light rays in order to reduce divergence of light.

Scanner and receiver 20 includes a motor 44, a mirror 46, a 90° mirror or prism 48 and a receiving telescope 50. Motor 44 rotates mirror 46 thus projecting light (designated by dashed-line arrows) entering scanner and receiver 20 in a 360° arc as the mirror rotates. Returning scattered light (designated by solid-line arrows) is reflected by mirror 46 into receiving telescope 50 which gathers the scattered light and directs it into a light detector 52 through a conventional filtration system 53. Filtration system 53 permits detection by detector 52 of light only in a selected bandwidth. Detector 52 converts the detected light into an electrical signal which is placed on a cable 54 for analysis by computer 24 (in FIG. 1). Detected light from other remote stations is likewise converted to signals which are placed on cables 56, 58, 60—one cable being connected to each remote station.

In operation, the light output of laser 14 is directed into one of objective lens 28, 30, 32, 34 by switching beam-director 26. A beam-director control 62 can be programmed to place the entire light output of laser 14 onto a selected objective lens. Alternatively, the control may be set to rapidly switch the light output from one selected lens to another. It is to be appreciated that the laser light output itself may be pulsing at a selected frequency and that when the beam-director places the laser output onto an objective lens, the scanner output likewise pulses.

Beam-director 26 and its associated control 62 are not necessary to permit proper functioning of the instant embodiment of the invention. It is possible to simply allow the light output of laser 14 to fall on all of the objective lenses simultaneously when using a cylindrical lens in place of the beam director control. Such an arrangement provides light on each of the fiberoptic cables and permits scanning and receiving of scattered light at each remote station; however, it is apparent that when the laser light output is split among the different cables, each is using light at a lower energy level so that received information is therefore reduced. Use of the beam-director permits directing the entire laser output onto a cable for transmission to each remote station, one at a time, and thus permits increased scanning and detection capabilities at each station.

Fiberoptic cables 16, 36, 38, 40 transmit the laser light output (when such is directed into that cable's associated objective lens) to their associated remote stations, like station 18. When the light arrives at station 18, collimator 42 (best seen in FIG. 2) directs it to scanner and receiver 20. The light output is projected from scanner and receiver 20 in a 360° arc by mirror 46. Scattered light returning to scanner and receiver 20 (indicated by solidline arrows) is collected by receiving telescope 50 and projected onto light detector 52 through filtration system 53. The light detector converts information relating to the scattered light into an electric signal which is placed on cable 54 for transmission to computer 24. Although the above description relates to station 18 it is to be appreciated that each of the other stations (not shown) function in a similar manner and provide information relating to their scanning area to computer 24 in the same manner as station 18.

One existing light detection and ranging scheme which might be used in accordance with the instant embodiment of the invention is differential absorption of scattered energy (DASE). When utilizing the DASE technique to monitor $NO_2$ levels in the atmosphere, laser 14 is a flash lamp pumped dye laser which emits either alternate or simultaneous light pulses at wavelengths of 4478.5 angstroms and 4500 angstroms. The 4478.5 angstrom pulse is at the peak absorption level of $NO_2$ while the 4500 angstrom pulse is at a lower absorption level. By separately filtering backscattered light via filtration system 53 to detect each of the transmitted wavelengths, and by comparing the amount of backscattered light detected at each frequency, both the position and the amount of $NO_2$ in the atmosphere may be determined. In addition to this DASE technique of monitoring pollution, other known techniques such as fluorescence, raman, resonance raman, longpath absorption, etc., are equally suited for use with the instant embodiment of the invention.

The instant embodiment of the invention has been shown with the scanner and receiver illustrated in FIG. 2. Other scanning and/or receiving apparatus known in the art are equally well suited for use with the invention. For example, in its simplest form, station 18 may include only a collimator, for projecting laser light output directly into the sky, and a light detector for sensing scattered laser light.

Use of the instant invention to monitor ambient levels of pollution creates a three-dimensional time-varying "map" of ambient pollution levels in computer 24. Such a map is generated by placing stations, like station 18, at locales where monitoring is desired and providing the light detector output at each station to a central computer, like computer 24. Such a map is generated despite the presence of topographical features, e.g., hills, trees, smokestacks, etc., which might block laser light, since the remote stations are selectively placed to avoid such light blocking.

It will be understood that modifications may be made from the instant embodiment of the invention which are within the spirit and scope of the following claims.

What is claimed is:

1. In light detection and ranging apparatus for monitoring pollution levels which includes a light source for scattering light from airborne pollution particles in order to derive information relating to the particles.
   a plurality of fiberoptic cables, each having one end adjacent the light source and the light output of the other end aimed at such particles;
   a light receiver for each cable, said receiver being constructed to detect light scattered by the particles at which its associated cable light output is aimed and to generate a signal indicative of a characteristic of the scattered light; and
   an information processor connected to each receiver, said processor adapted to evaluate said receiver signals in order to derive information relating to the airborne particles.

2. The apparatus of claim 1 wherein said apparatus further includes a beam-director interposed between said light source and said adjacent cable ends, said beam-director being constructed to selectively couple the output of said light source to each of said cable ends.

3. The apparatus of claim 2 wherein said apparatus further includes control means connected to said beam-director, said control means being adapted to rapidly sequentially couple said light source output to each cable end, thereby enabling said processor to develop a three-dimensional time-varying map of the volume at which the cable light output is aimed.

4. In a method of light detection and ranging to monitor airborne particles using the step of scattering the light of a single source from such particles, the step of:
   directing said light into the ends of a plurality of fiberoptic cables;
   aiming the light output of the other end of said cables at such particles;
   aiming one receiver for each cable at such particles so that each receiver detects scattered light originating from its associated cable; and
   using said detected light to generate a signal which includes information relating to the airborne particles.

5. In the method of claim 4 including the steps of:
   rapidly, sequentially coupling said directed light into the ends of the plurality of fiberoptic cables; and
   processing said detected light to develop a three-dimensional time-varying map of the volume of said airborne particles.

* * * * *